(12) United States Patent
Shibamoto et al.

(10) Patent No.: US 8,717,848 B2
(45) Date of Patent: May 6, 2014

(54) ULTRASOUND PROBE

(75) Inventors: Koichi Shibamoto, Nasushiobara (JP);
Hiroyuki Shikata, Nasushiobara (JP);
Minoru Aoki, Nasushiobara (JP);
Takashi Takeuchi, Otawara (JP)

(73) Assignees: Kabushiki Kaisha Toshiba, Tokyo (JP);
Toshiba Medical Systems Corporation, Tochigi-Ken (JP)

( * ) Notice: Subject to any disclaimer, the term of this patent is extended or adjusted under 35 U.S.C. 154(b) by 0 days.

(21) Appl. No.: 13/509,842

(22) PCT Filed: Nov. 24, 2011

(86) PCT No.: PCT/JP2011/077040
§ 371 (c)(1),
(2), (4) Date: May 15, 2012

(87) PCT Pub. No.: WO2012/070613
PCT Pub. Date: May 31, 2012

(65) Prior Publication Data
US 2013/0229893 A1    Sep. 5, 2013

(30) Foreign Application Priority Data
Nov. 25, 2010    (JP) ................................ 2010-262471

(51) Int. Cl.
*A61B 8/00*        (2006.01)
*H04R 1/20*        (2006.01)

(52) U.S. Cl.
USPC ....................................................... 367/140

(58) Field of Classification Search
USPC .................................. 367/140, 152; 600/459
See application file for complete search history.

(56) References Cited

U.S. PATENT DOCUMENTS

| | | |
|---|---|---|
| 2001/0021807 A1 | 9/2001 | Saito et al. |
| 2006/0232164 A1 | 10/2006 | Kondo et al. |
| 2009/0062655 A1 | 3/2009 | Saito |
| 2012/0004554 A1* | 1/2012 | Aoki et al. ................... 600/459 |
| 2012/0253199 A1* | 10/2012 | Aoki ............................. 600/459 |
| 2013/0226006 A1* | 8/2013 | Tsuzuki ........................ 600/459 |
| 2013/0229893 A1* | 9/2013 | Shibamoto et al. ........... 367/140 |

FOREIGN PATENT DOCUMENTS

| | | |
|---|---|---|
| JP | 61-169100 A | 7/1986 |
| JP | 2001-245883 A | 9/2001 |
| JP | 2007-288396 A | 11/2007 |
| JP | 2007-319597 A | 12/2007 |
| WO | 2004/075753 A1 | 9/2004 |
| WO | 2007/088772 A1 | 8/2007 |
| WO | WO 2012070613 A1 * | 5/2012 |

OTHER PUBLICATIONS

International Search Report for corresponding PCT/JP2011/077040 mailed on Jan. 10, 2012.

* cited by examiner

*Primary Examiner* — Daniel Pihulic
(74) *Attorney, Agent, or Firm* — Yoshida & Associates, LLC

(57) ABSTRACT

An ultrasound probe is provided that may improves specific desensitization of the frequency observed in the frequency characteristics and/or directional characteristics. The ultrasound probe related to this embodiment comprises an ultrasound transducer 10 and a plurality of acoustic matching layers 20 arranged in layers in the direction of irradiation irradiated from the ultrasound transducer 10, wherein, the plurality of acoustic matching layers 20 form a film and each of the adjacent acoustic impedance of longitudinal waves is substantially the same and has a different Poisson's ratio.

8 Claims, 14 Drawing Sheets

ULTRASOUND PROBE

CROSS-REFERENCE TO RELATED APPLICATIONS

This application is based upon and claims the benefit of priority from Japanese Patent Applications No. 2010-262471, filed Nov. 25, 2010; the entire contents of all of which are incorporated herein by reference.

FIELD

Embodiments of the present invention relate to an ultrasound probe that allows improvement of the directional characteristics of the elements in the ultrasound probe.

BACKGROUND

Ultrasound diagnostic equipment scans the inside of the subject with ultrasound waves and images the internal state of the subject based on received signals generated from reflected waves inside the subject.

Ultrasound diagnostic equipment such as this transmits ultrasound waves from an ultrasound probe to inside the subject, receives reflected waves generated from acoustic impedance mismatching inside the subject, and generates received signals. The ultrasound probe generates ultrasound waves by oscillating based on the transmitted signal and arranges in a scanning direction a plurality of ultrasound transducers that generate receiving signals by receiving reflected waves in an array configuration (for example, Patent literature 1).

The main configuration of conventional ultrasound probes is explained with reference to FIG. 11. Included is an ultrasound transducer 10 generating ultrasound waves, an acoustic matching layer (ML: Matching Layer) 20 reducing the acoustic impedance (AI) mismatch between the ultrasound transducer 10 and a living body from the ultrasound transducer 10 to the biological contact surface side, and an acoustic lens 30 converting the ultrasound waves. Moreover, from the ultrasound transducer 10 to the cable side, there is a substrate for signal withdrawal (FPC: Flexible Print Circut) 40 and backing material 50.

The acoustic matching layer 20 is established in 2 to 3 layers while gradually lowering the acoustic impedance AI from the ultrasound transducer 10 to the living body. ¼ wavelength λ is widely used as the thickness of respective acoustic matching layers 20. Here, the wavelength λ is the wavelength of ultrasound waves that transmit respective acoustic matching layers 20. Generally, materials with high acoustic impedance AI are hard and have good cutting ability; therefore, in order to reduce acoustic coupling with the adjacent elements, the acoustic matching layer 20 is simultaneously divided when the ultrasound transducer 10 is divided; however, materials with low acoustic impedance AI have poor cutting ability and slow sound speed, so the shape ratio (w/t) cannot be sufficiently reduced. Here, w is the width and t is the thickness. When w/t is close to 1, longitudinal waves are converted to transversal vibrations in the acoustic matching layer 20 within a marginal zone and interference between the two becomes unwanted vibrations, negatively influencing the transmission and reception characteristics of the ultrasound waves.

DETAILED DESCRIPTION

To solve the problems mentioned above, the ultrasound probe according to embodiments comprises the ultrasound transducer and a plurality of acoustic matching layers arranged by layering in the direction of irradiation of the ultrasound waves irradiated from the ultrasound transducer. The plurality of acoustic matching layers are shaped like a film and substantially are same in the acoustic impedance of longitudinal waves of the adjacent acoustic matching layer. The Poisson's ratio of the plurality of acoustic matching layers are respectively different.

Next, the ultrasound probe related to this embodiment is explained based on each diagram.

Figure 1:
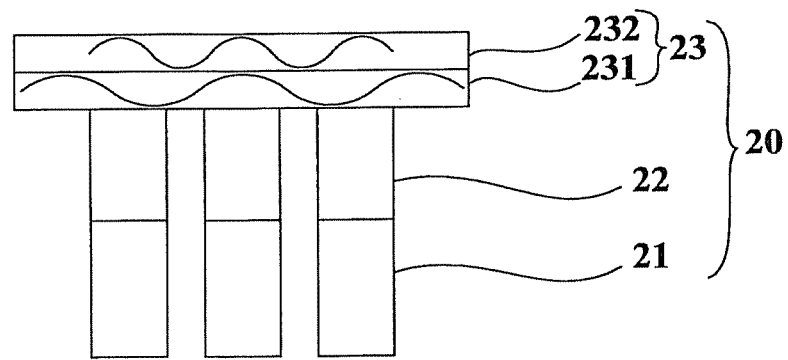
FIG. 1 is a diagram of the acoustic matching layer of the ultrasound probe pertaining to the embodiment.
Figure 2:
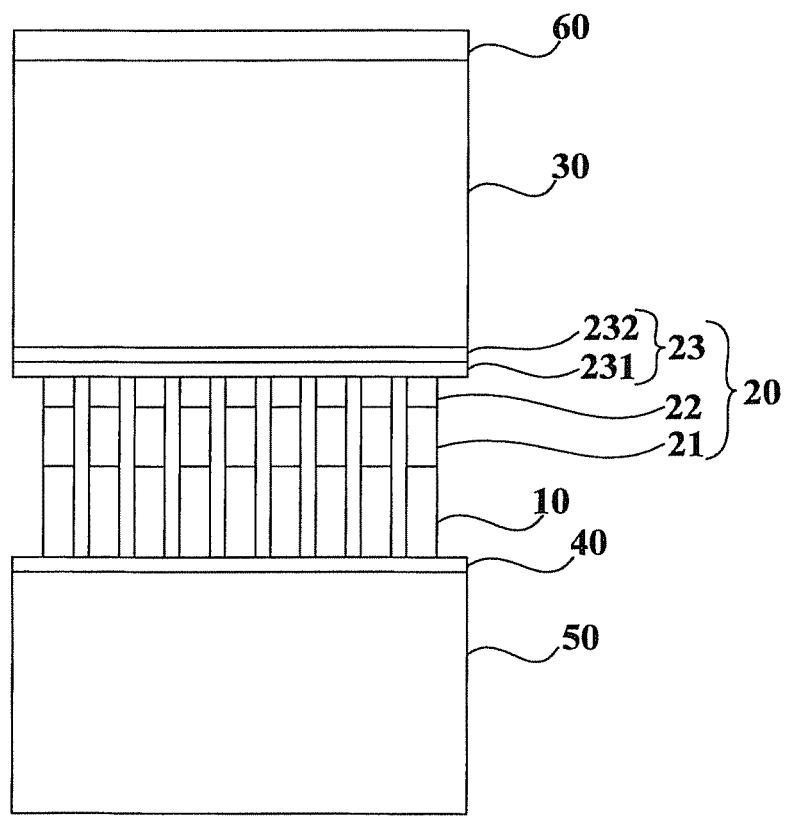
FIG. 2 is a diagram of the simulation model.

First, the configuration of the ultrasound probe is described with reference to FIG. 1 and FIG. 2. FIG. 1 is a diagram of the acoustic matching layer of the ultrasound probe pertaining to the embodiment; FIG. 2 is a diagram of the simulation model.

The ultrasound probe comprises an ultrasound transducer 10 transceiving the ultrasound waves, an acoustic matching layer (ML) 20, an acoustic lens 30 focusing the ultrasound waves transceived from the ultrasound transducer 10, a substrate for signal withdrawal (FPC) 40, and a backing material 50 which arranged in the rear of an ultrasound transducer 10 and which suppresses excess oscillations by absorbing transmissions to the rear.

The ML 20 is used to acoustically match the ultrasound transducer 10 and the acoustic lens 30, wherein, the first acoustic matching layer 21, the second acoustic matching layer 22, and the third acoustic matching layer 23 are arranged in layers in the direction of irradiation of ultrasound waves irradiated from the ultrasound transducer 10.

The ultrasound transducer 10, the first acoustic matching layer 21, and the second acoustic matching layer 22 are all separated and arranged in arrays.

The third acoustic matching layer 23 comprises two layers, the upper and the lower. The third acoustic matching layer 231 of the lower layer side and the third acoustic matching layer 232 of the upper layer side are each shaped like a film. Hereinafter, the third acoustic matching layer 23, the third acoustic matching layer 231 of the lower layer side, and the third acoustic matching layer 232 of the upper layer side may respectively be referred to as a film-like ML.

In the case of the film-like ML, a film-like ML with adhesive lamination unified as multiple layers is used (refer to FIG. 1). In concrete terms, example of materials includes polyethylene and polyurethane. Each of materials approximately coincides in acoustic impedance of longitudinal waves AI and has different Poisson's ratio ($\sigma$). These materials are configured by adhesively laminating. Regarding the entire thickness, $\lambda/4$ is maintained. The frequency of the standing wave, in which conflict with the adjacent element occurs, is set off while maintaining the role of acoustic matching to suppress resonations causing unwanted vibrations. Furthermore, longitudinal ultrasound waves occur in orthogonal direction to the surface of the ultrasound transducer 10 and transverse waves occur orthogonally to orthogonal direction. Generally, regarding the effect of acoustic impedance on transmission and reception characteristics, acoustic impedance of longitudinal waves AI and acoustic impedance of transverse waves AI must be taken into consideration; however, in the case of the film-like ML, the acoustic impedance of transverse waves AI is small compared to the acoustic impedance of longitudinal waves AI regarding the effect on transmission and reception characteristics, so materials, etc. for film-like ML are selected taking into consideration the acoustic impedance of longitudinal waves AI alone.

[Simulation]

The effect of this ultrasound probe was confirmed with a sound simulation by using finite element analysis. The model used for sound simulation is shown in FIG. 2. Regarding the simulation, a center frequency of 5 MHz and a sector array transducer of the element pitch of 0.12 mm were assumed, and it was made into a simple model with the ultrasound transducer 10, acoustic matching layer 20, acoustic lens 30, FPC40, and backing material 50 alone.

The film-like ML to be layered is polyethylene (Poisson's ratio 0.435) and polyurethane (Poisson's ratio 0.486) having the acoustic impedance of the longitudinal waves AI with approximately 2.0. The polyethylene with a small Poisson's ratio is arranged on the ultrasound transducer 10 side. The polyurethane with a large Poisson's ratio is arranged on the acoustic lens 30 side. Moreover, as the film-like ML to be layered, a material with a Poisson's ratio within the range of 0.35-0.49 and with acoustic impedance of longitudinal waves AI within the range of 1.5-5.0 [Mrayl] may be used. Here, 1.0 [Mrayl] corresponds to 106 [$kgm^{-2}s^{-1}$].

The thickness of the layered film-like ML is made substantially ¼ the wavelength $\lambda$ predetermined by the frequency (5 MHz) in the same manner as the thickness of the proposed film-like acoustic matching layer 20. In the model of this array transducer, only one element of the center was driven by the impulse waveform, while simulation was conducted for the process of ultrasound wave transmission and the action of elements.

[Results of the Simulation]

Figure 3:
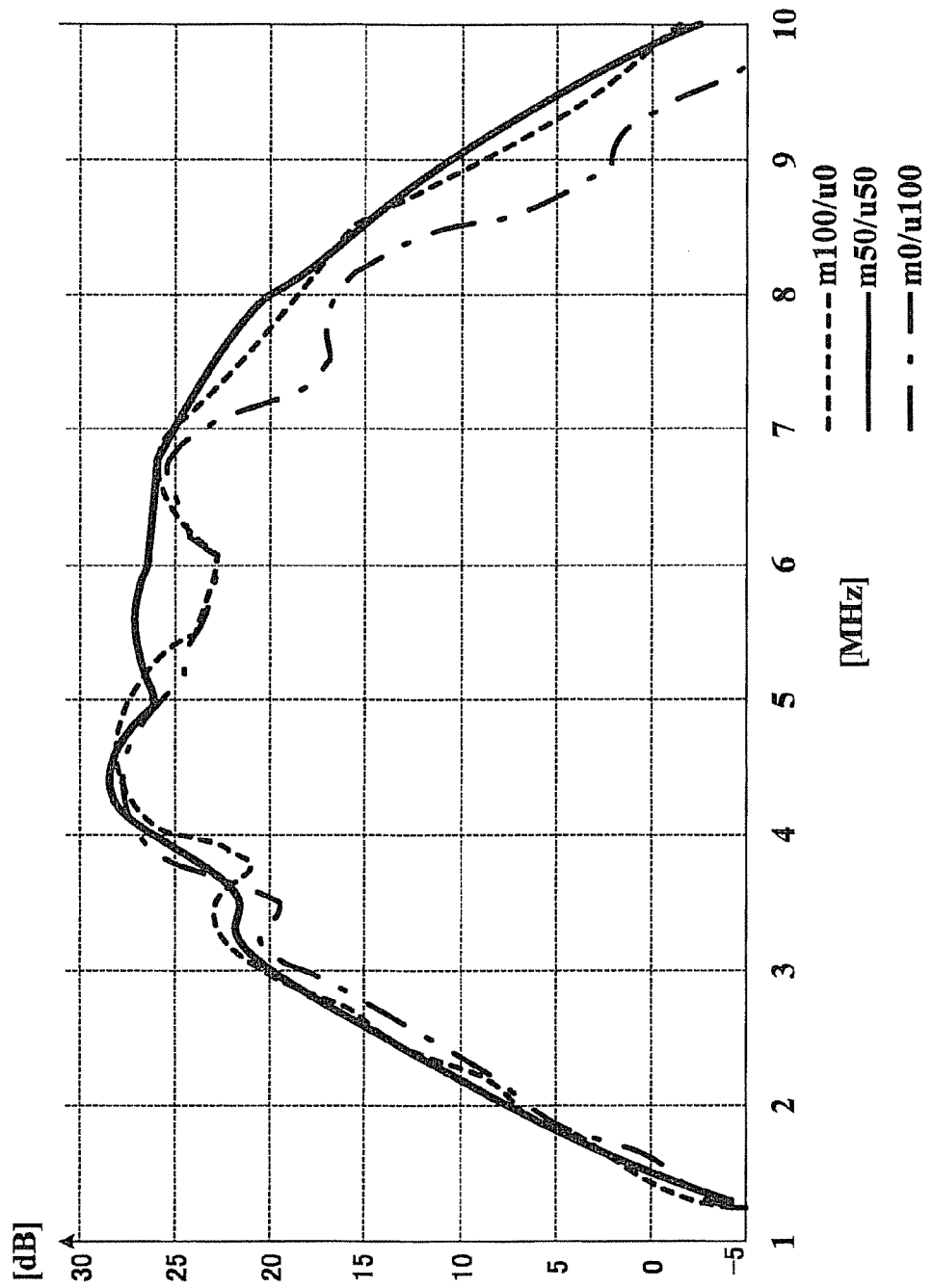
FIG. 3 is a diagram of the transmission bandwidth.
Figure 5:
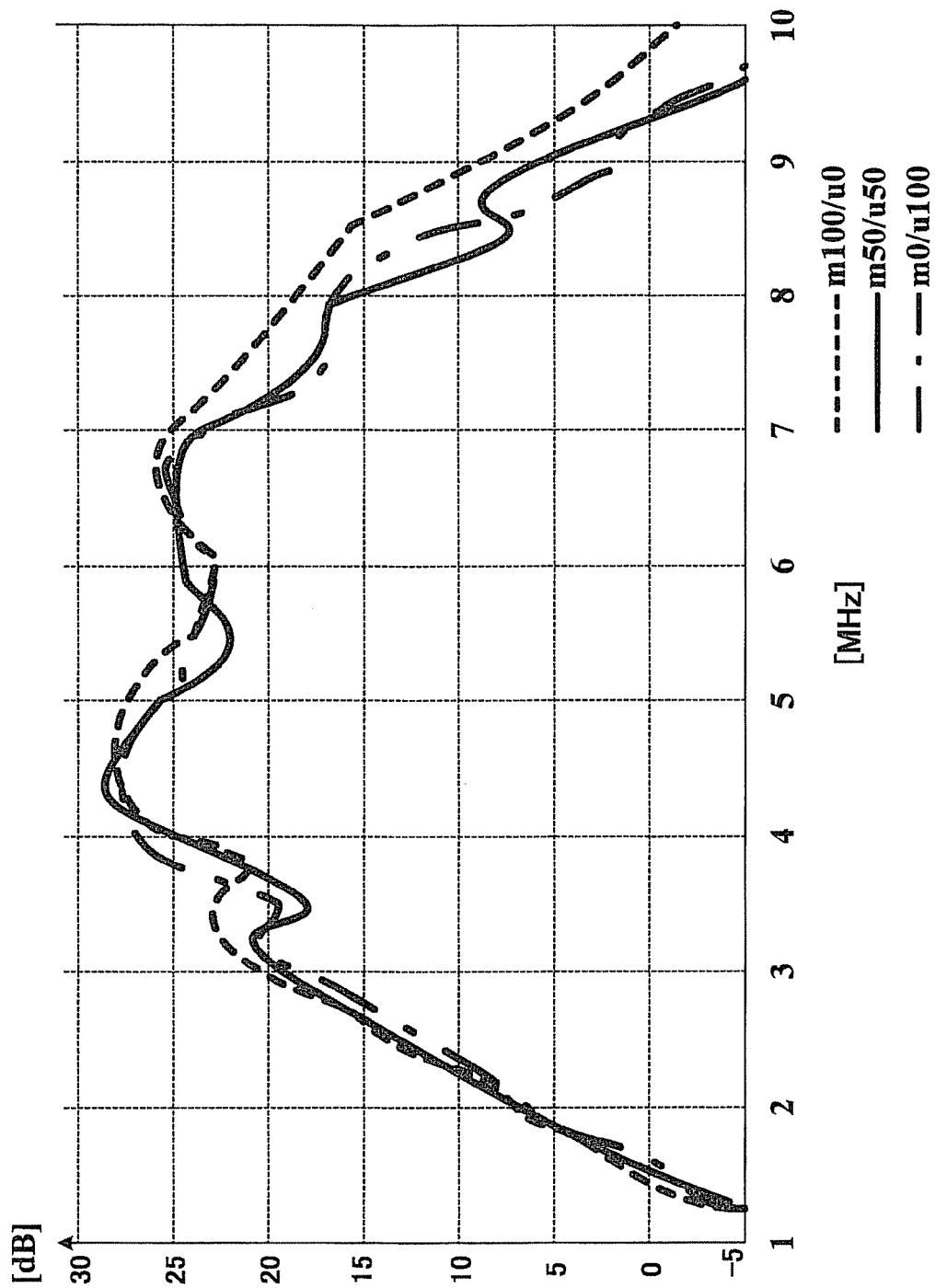
FIG. 5 is a graph of the transmission bandwidth to investigate the order of the film.
Figure 6:
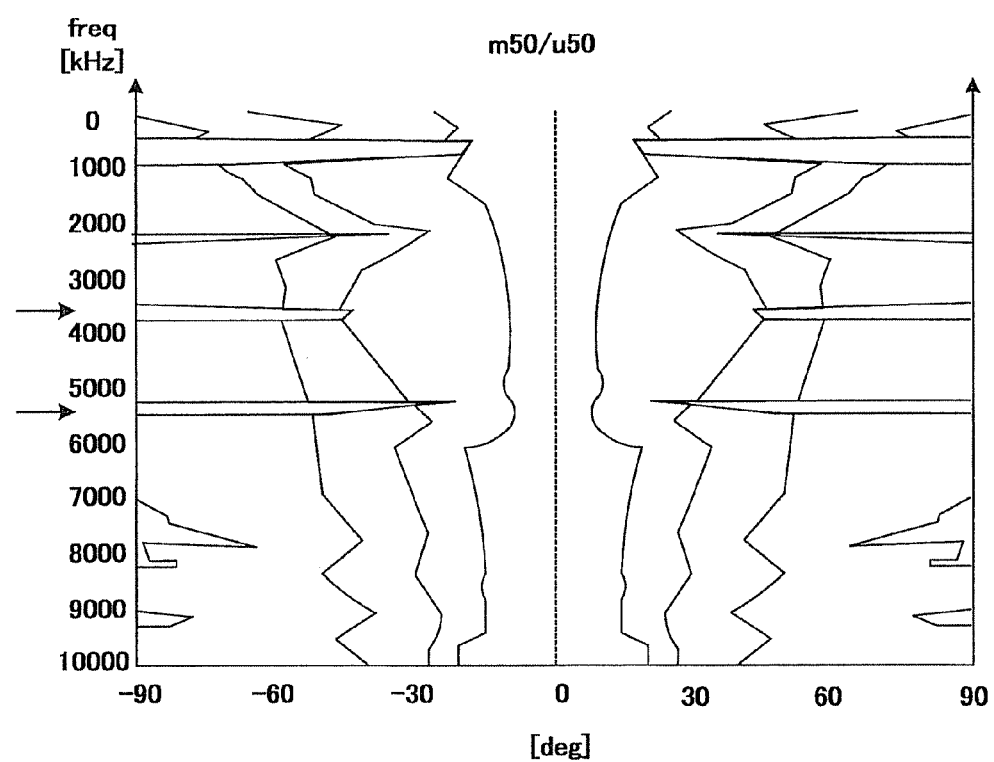
FIG. 6 is a diagram of the element factor in order to investigate the order of the film.

The results of the simulation are explained with reference to FIG. 3 to FIG. 6. FIG. 3 is a diagram illustrating the frequency characteristics calculated from a time waveform of sound pressure at the tip of the acoustic lens 30, FIG. 4 is a diagram showing the directional characteristics (EF) of the driver element, the diagram contour-displaying the gain of received signals 0 to −30 dB, FIG. 5, is a diagram showing the transmission bandwidth in order to investigate the order of the film, and FIG. 6 is a diagram showing the element factor in order to investigate the order of the film and is a diagram counter-displaying gain of received signals 0 to −30 dB.

In FIG. 3, the frequency bandwidth 1 to 10 [MHz] is provided on the longitudinal axis, and the gain of received signals [dB] is provided on the transverse axis. In FIG. 3, m100/u0: the film-like ML is polyethylene alone, m0/u100: the film-like ML is polyurethane alone, m50/u50: the film-like ML is the polyethylene/polyurethane of which thickness ratio of the film-like ML indicates 50:50.

Figure 4A:
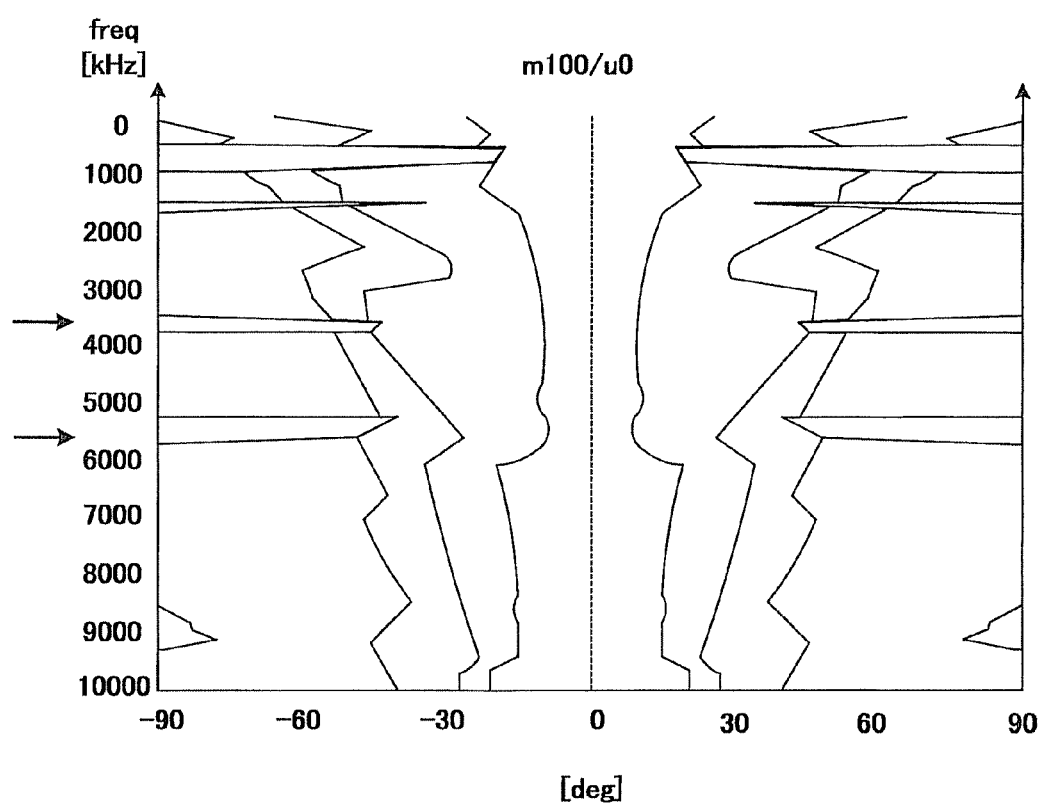
FIG. 4A is a diagram of the element factor when the thickness ratio of polyethylene/polyurethane is 100:0.
Figure 4B:
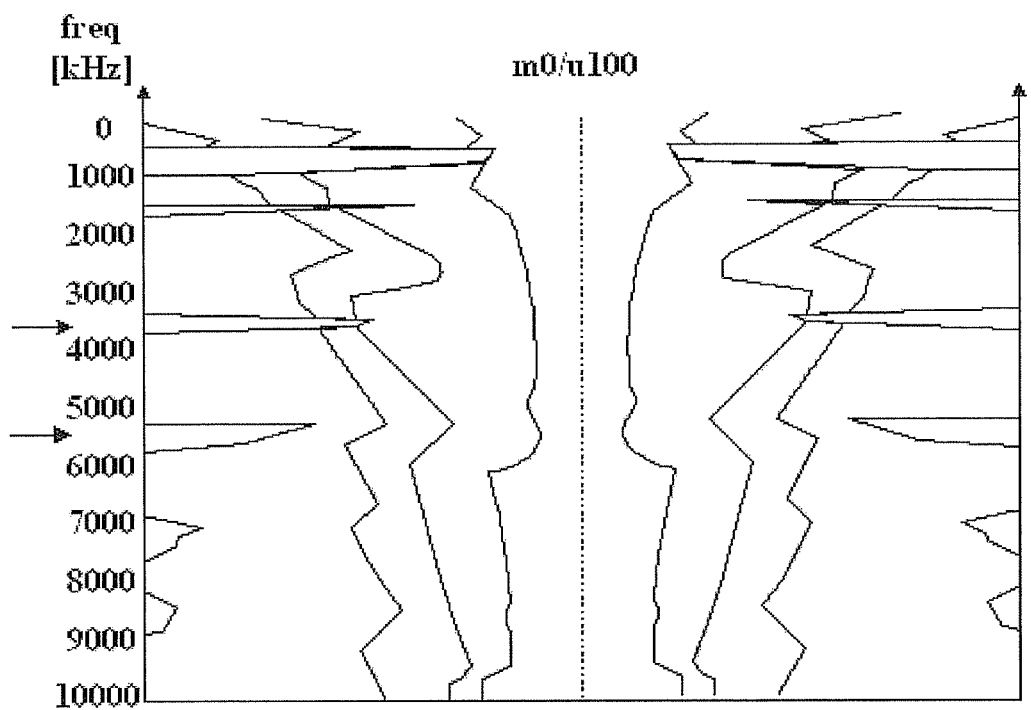
FIG. 4B is a diagram of the element factor when the thickness ratio of polyethylene/polyurethane is 0:100.
Figure 4C:
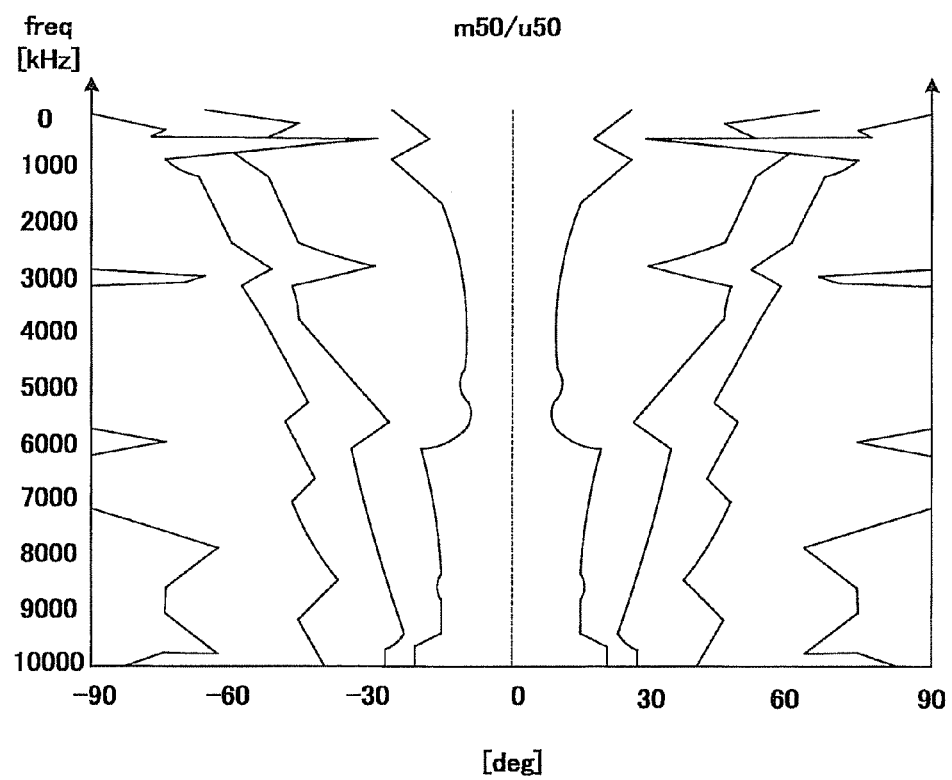
FIG. 4C is a diagram of the element factor when the thickness ratio of polyethylene/polyurethane is 50:50.

The respective results of m100/u0, m0/u100, and m50/u50 are shown in FIG. 4A, FIG. 4B, and FIG. 4C. In FIG. 4A to FIG. 4C, a scanning angle of −90° to 90° [deg] is provided on the longitudinal axis, while a frequency bandwidth of 0 to 10,000 [kHz] is provided on the transverse axis.

From these results, if the film-like ML consists of a single material alone such as polyethylene, polyurethane, etc., a frequency with a specifically low sensitivity is present (for example, near 3.8 MHz, 5.5 MHz) (Shown by → in FIG. 4A, FIG. 4B). In other words, it may be understood that a dip is present in the frequency characteristic.

Moreover, when the film-like ML is layered, it may be understood that this effect is being eased. For example, in m50/u50, the dip observed in the frequency characteristic and directional characteristics (EF) was suppressed, so it may be observed that desensitization of specific frequencies is improved. (Refer to FIG. 4C).

Furthermore, a configuration is taken that reverses the film-like ML to be layered, that is to say, when a polyurethane with a large Poisson's ratio is arranged on the ultrasound transducer 10 side and the polyethylene with a small Poisson's ratio is arranged on the acoustic lens 30 side, the dip is not eased as seen in the stimulation results of the frequency characteristic (Refer to FIG. 5) and directional characteristics (EF) (refer to FIG. 6), and it may be understood that the expected results cannot be obtained. In the accumulated film-like ML, it is necessary to arrange materials with small Poisson's ratios on the ultrasound transducer 10 side, and to arrange materials with large Poisson's ratios on the acoustic lens 30 side.

[Embodiment of the Simulation]

[Embodiment 1]

Next, an embodiment 1 will be explained. A plurality of acoustic matching layers 20 comprising the film-like ML and acoustic lens 30 are present on the side of acoustic radiation of the ultrasound transducer 10, while FPC 40 and the backing material 50 are present on the rear side. As the film-like ML, a combination of two types of resin selected from materials with a low acoustic impedance of longitudinal waves AI, in concrete terms, polyethylene resin, polyurethane resin, polyimide resin, epoxy resin, polyester resin, etc., are used.

An example of the production method of the ultrasound probe in order to realize this embodiment is shown. Here, a sector array probe is determined as the representative embodiment.

First, the ultrasound transducer 10 and the acoustic matching layer 20 other than film-like ML and are layered. The FPC40 and the backing material 50 are attached to them.

Generally, a glued connection using epoxy adhesives is typical as an adhesive. From the above, the layered structure of the acoustic matching layer 20 other than film-like ML, ultrasound transducer 10, FPC 40, and the backing material 50 are prepared from the side of acoustic irradiation. After making this layered structure as a device array by dicing from the acoustic matching layer 20 side, the film-like ML is adhesively layered. The layered film-like ML has substantially the same acoustic impedance of longitudinal waves AI and is a material with a different Poisson's ratio, in which a small material (for example, the polyethylene) is arranged on the ultrasound transducer 10 side, while a small material (for example, the polyurethane) is arranged on the acoustic lens 30 side.

The total thickness of the two upper and lower layers of the film-like ML is ¼ the wavelength λ of the ultrasound waves transmitted to the film-like ML, while the thickness ratio of the polyethylene and polyurethane is determined to be uniform (substantially 1). Moreover, the two upper and lower film-like ML layers may be adhesively layered to the element after adhesively layering in advance or they may be adhesively layered to the element one by one in order. Finally, the acoustic lens 30 is joined and the ultrasound probe is completed.

[Embodiment 2]

Figure 7:
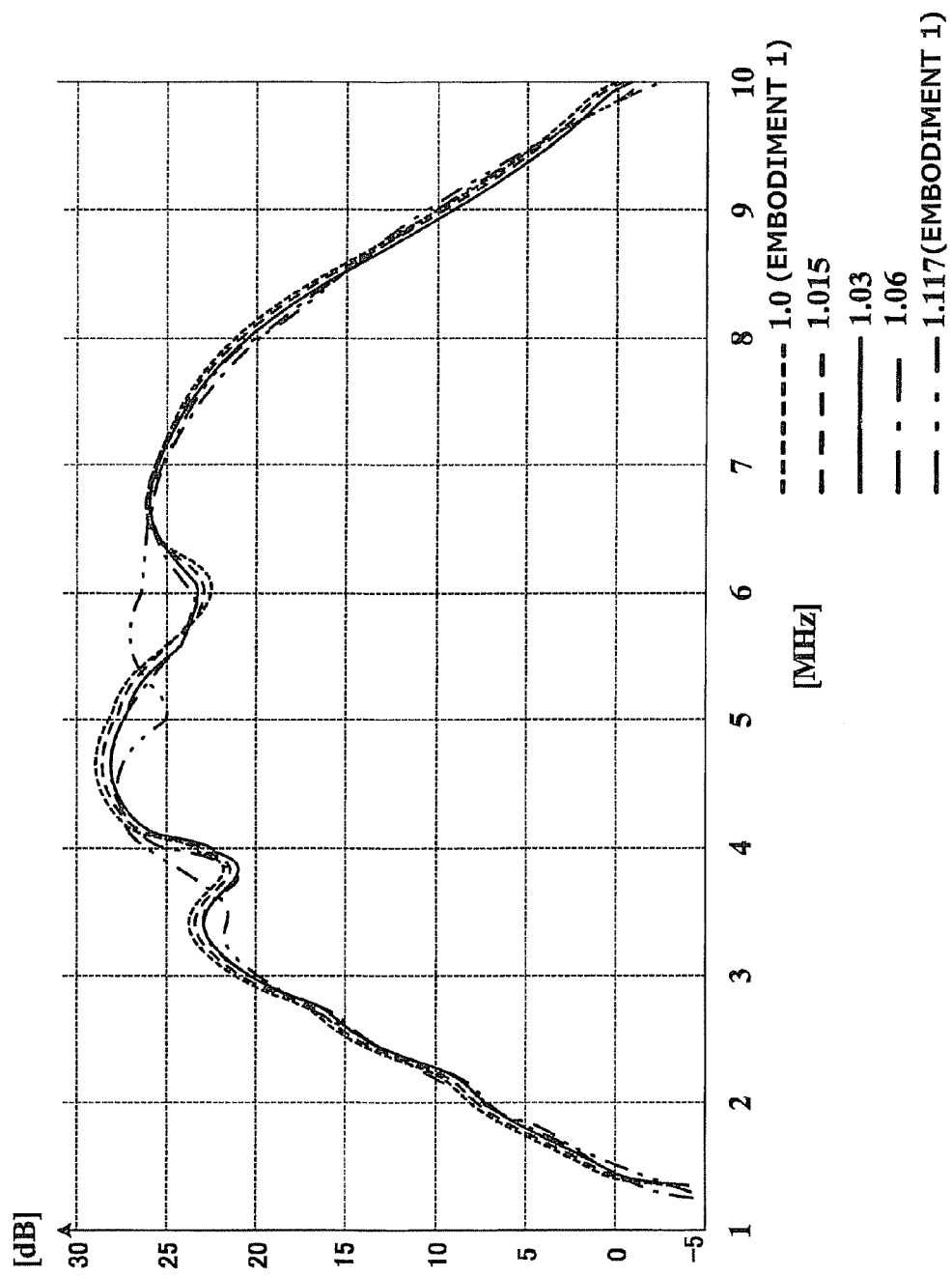
FIG. 7 is a graph of the transmission bandwidth in order to investigate the Poisson's ratio.
Figure 8A:
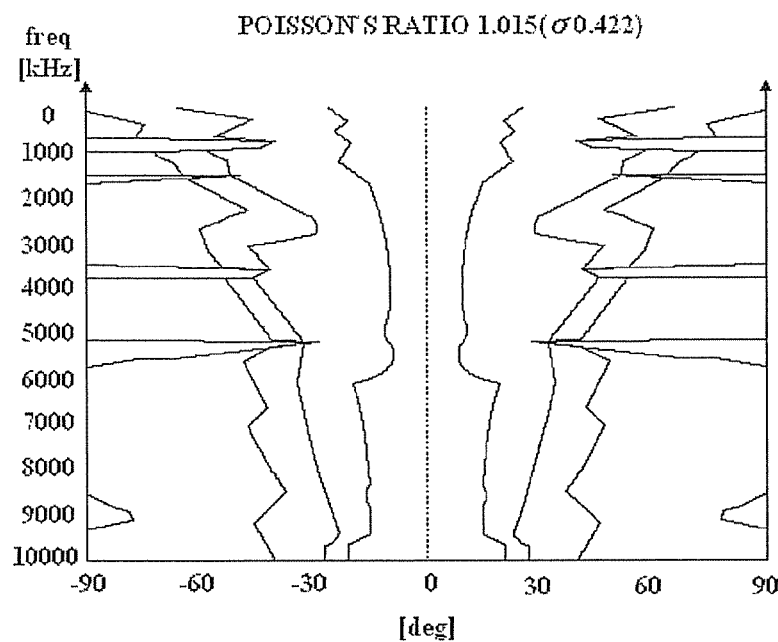
FIG. 8A is a diagram of the element factor when the Poisson's ratio of polyurethane to polyethylene is 1.015.

Next, Embodiment 2 will be explained with reference to FIG. 7 and FIG. 8. FIG. 7 is a diagram of the transmission bandwidth in order to investigate the Poisson's ratio, while FIG. 8 is a diagram of the element factor in order to investigate the Poisson's ratio. The transmission characteristics are shown in FIG. 7, wherein the frequency bandwidth 1 to 10 [MHz] is provided on the transverse axis, while gain of the received signal [dB] is provided on the longitudinal axis. In FIG. 8, the directional characteristics (EF) are shown, gains 0 to −30 dB of the received signal are contour-displayed, the scanning angle of −90° to 90° [deg] is provided on the transverse axis, and the frequency bandwidth 0 to 10,000 [kHz] is provided on the longitudinal axis.

The basic configuration is the same as in Embodiment 1. In Embodiment 1, the film-like ML was configured by layering polyethylene (σ0.435) and polyurethane (σ0.486); however, an effect expected may also be obtained by the combination of materials with a smaller difference in Poisson's ratio.

Here, the acoustic impedance of the longitudinal waves AI are all approximately 2.0, simulations perform with changed the Poisson's ratio σ of the polyurethane to the polyethylene (σ0.435) (as the Poisson's ratio, 1.0 (Embodiment 1 shown in FIG. 4A, FIG. 4B), 1.015, 1.03, 1.06, 1.117 (Embodiment 1 shown in FIG. 4C)) (refer to FIG. 7).

Figure 8B:
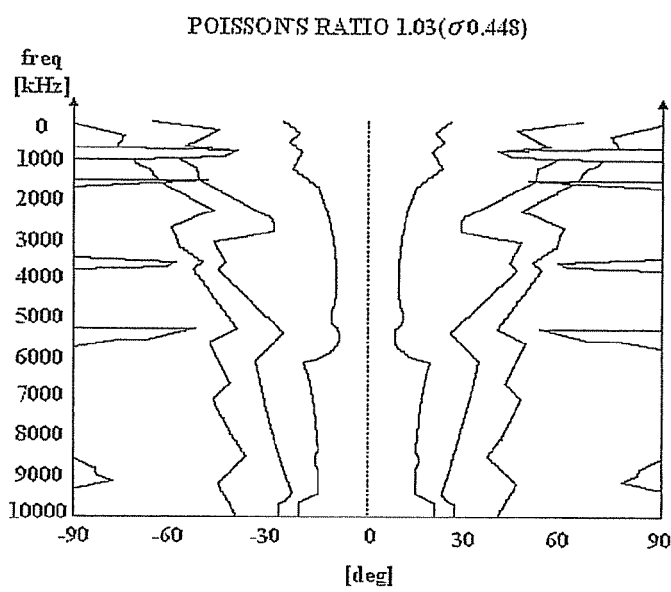
FIG. 8B is a diagram of the element factor when the Poisson's ratio of polyurethane to polyethylene is 1.03.
Figure 8C:
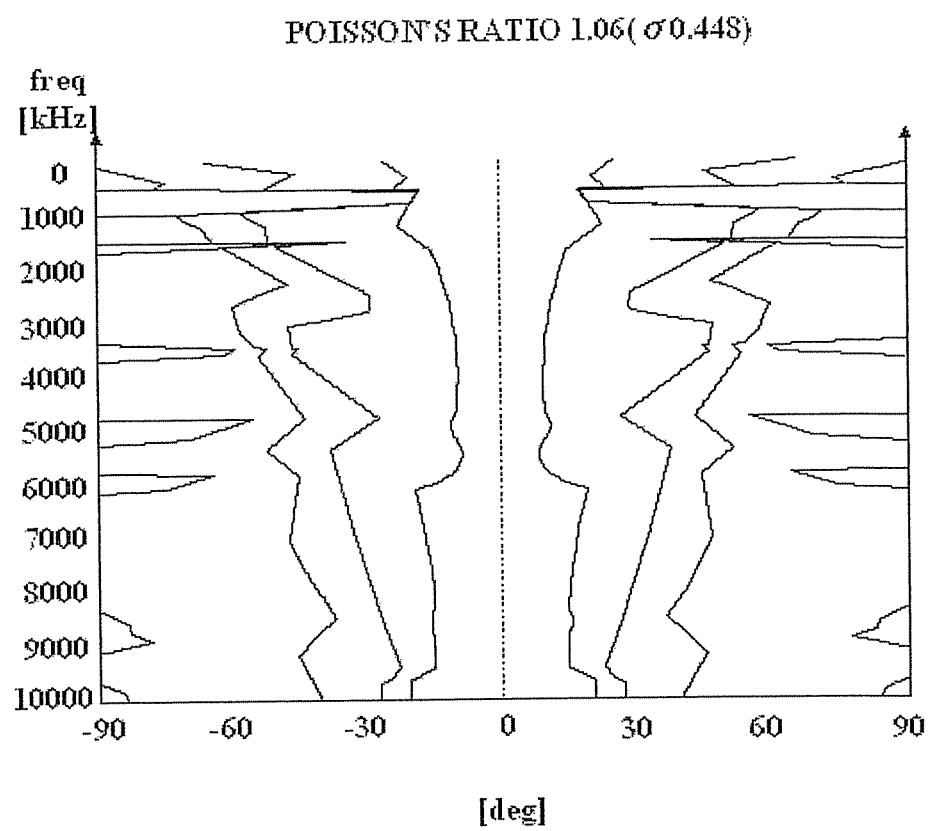
FIG. 8C is a diagram of the element factor when the Poisson's ratio of polyurethane to polyethylene is 1.06.

Compared to the results when the film-like ML is the only material (refer to FIG. 4, FIG. 5), the dip in the specificity is eased when the Poisson's ratio is 1.03 or more (refer to FIG. 8B, FIG. 8C). However, when the Poisson's ratio is 1.015, the difference in the Poisson rate of the laminating film-like ML is small; therefore, it may be understood that the effect of suppressing the standing wave is very small (in particular, the dip of 5.5 MHz has almost no change) (refer to FIG. 8A). From this result, the layering film-like ML is preferably configured with materials with 3% or more variation in the Poisson's ratio.

[Embodiment 3]

Figure 9:
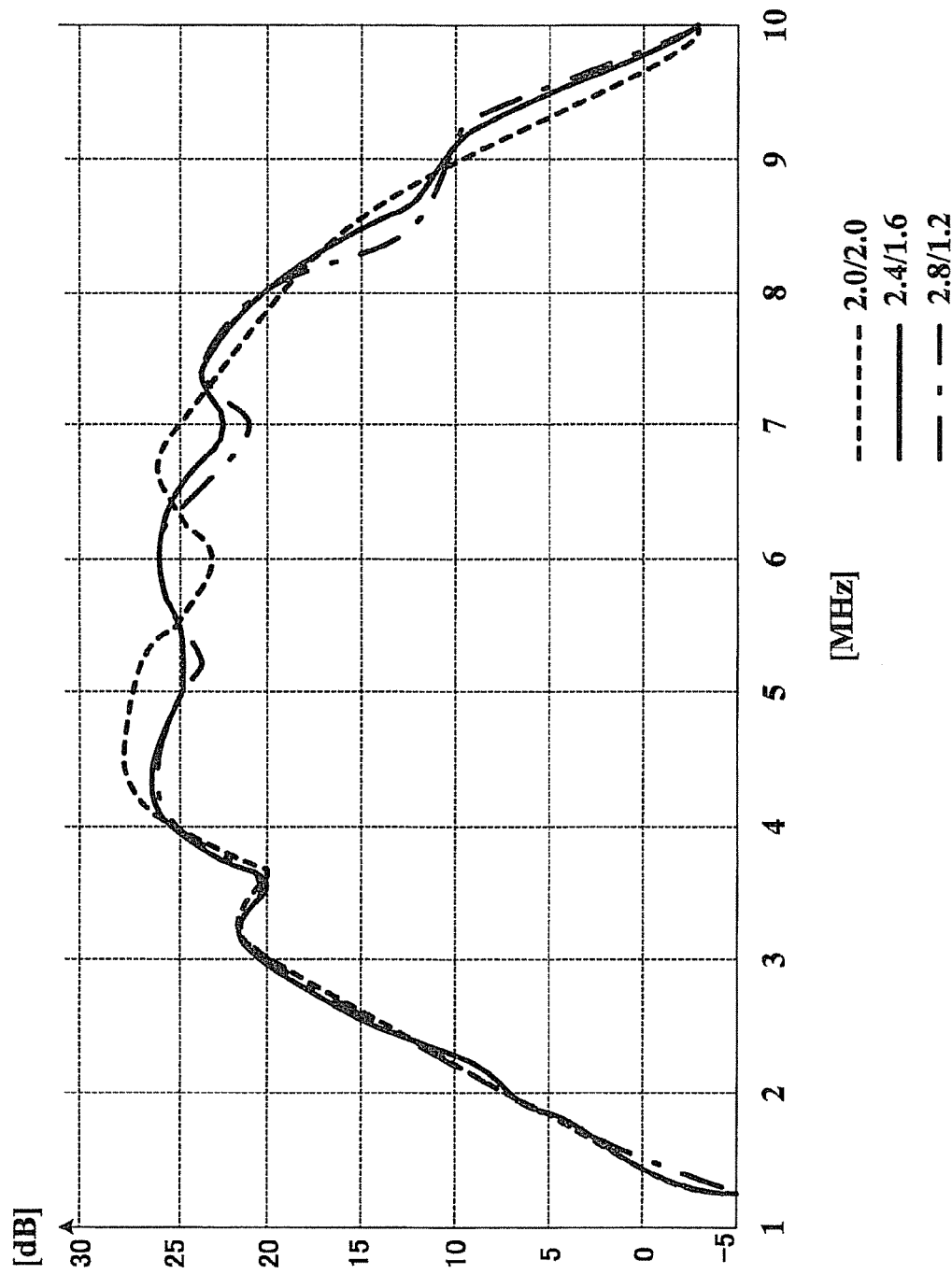
FIG. 9 is a graph of the transmission bandwidth in order to investigate the difference in the acoustic impedance of longitudinal waves.
Figure 10A:
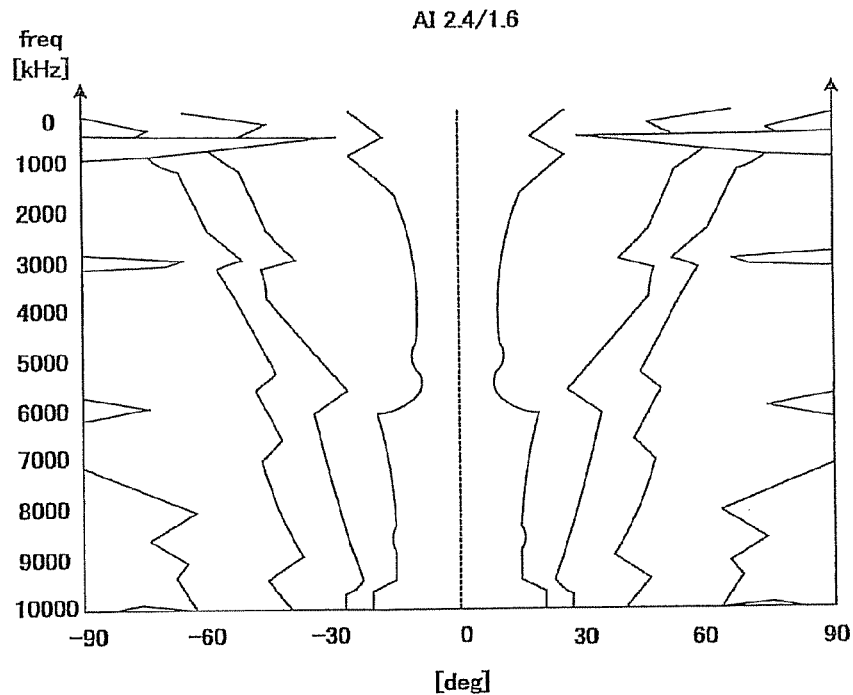
FIG. 10A is a diagram of the element factor when the acoustic impedance of longitudinal waves AI of the polyethylene/polyurethane is 2.4/1.6.

Next, Embodiment 3 is will be explained with reference to FIG. 9 and FIG. 10. FIG. 9 is a diagram of the transmission bandwidth in order to investigate the difference in acoustic impedance of longitudinal waves AI, while FIG. 10 is the element in order to investigate the difference in acoustic impedance of longitudinal waves AI. The transmission characteristics are shown in FIG. 9, with the frequency bandwidth 1 to 10 [MHz] provided on the transverse axis and the gain of the received signal [dB] provided on the longitudinal axis. In FIG. 10, the directional characteristics (EF) are shown, the gain 0 to −30 dB of the received signal are contour-displayed, the scanning angle of −90° to 90° [deg] is provided on the transverse axis, and the frequency bandwidth 0 to 10000 [kHz] is provided on the longitudinal axis.

The fundamental configuration is the same as in Embodiment 1. The film-like ML preferably comprises generally the same acoustic impedance of longitudinal waves AI for acoustic coordination; however, because the effect is small if the extent of change is small, the expected effect may be obtained. Here, a simulation was performed regarding a case in which the acoustic impedance of longitudinal waves AI of polyethylene/polyurethane is changed (2.0/2.0 (Embodiment 1), 2.4/1.6, 2.8/1.2) (refer to FIG. 9).

Figure 10B:
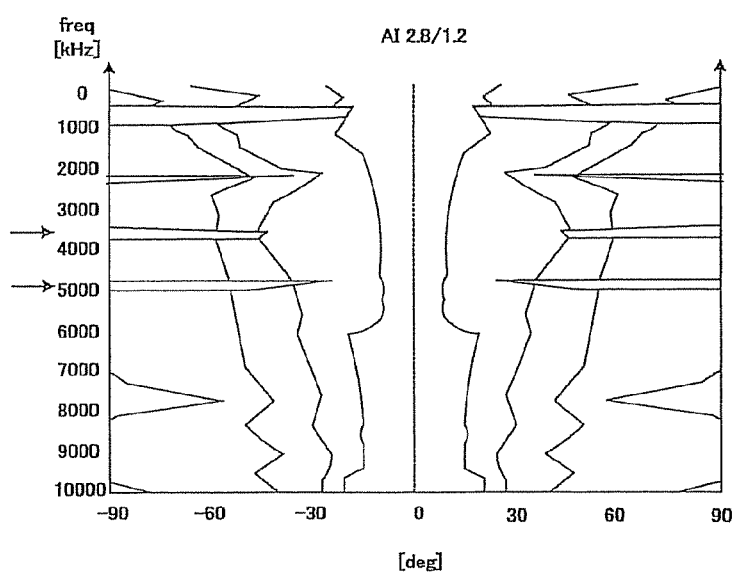
FIG. 10B is a diagram of the element factor when the acoustic impedance of longitudinal waves AI of the polyethylene/polyurethane is 2.8/1.2.
Figure 11:
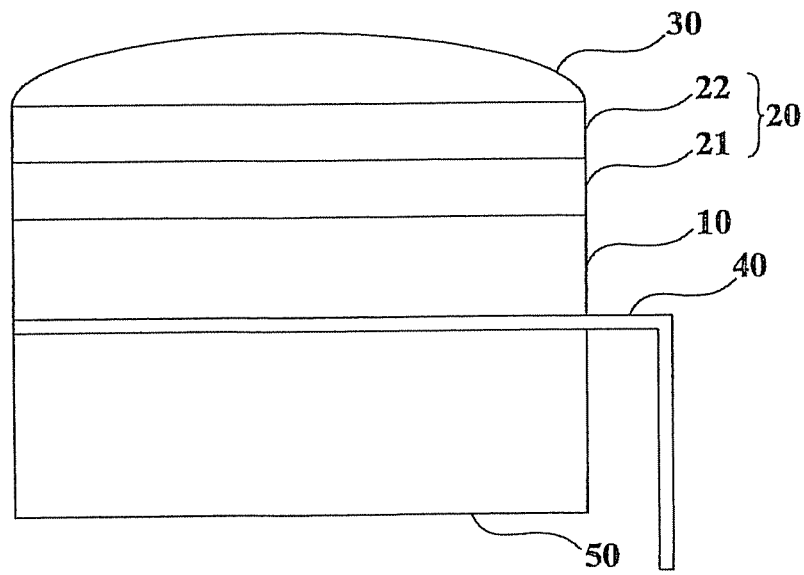
FIG. 11 is a cross-sectional view of a conventional ultrasound probe.
Figure 12:
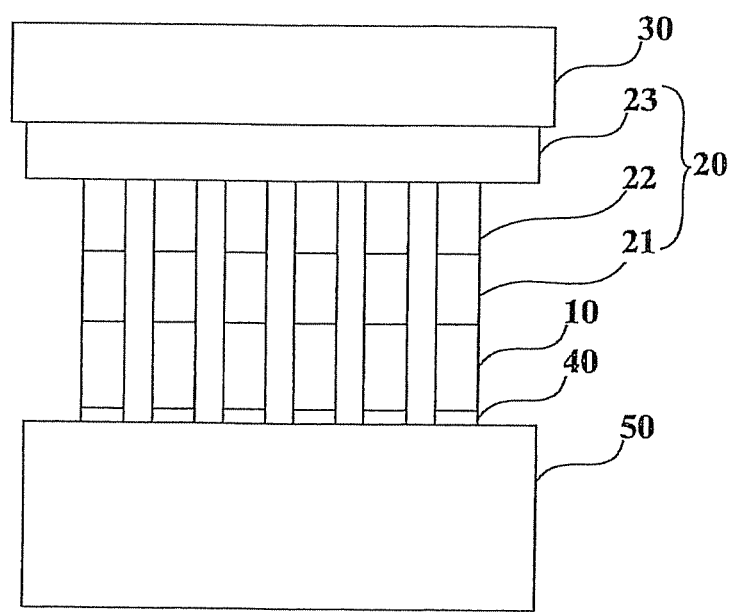
FIG. 12 is a cross-sectional view of the proposed ultrasound probe.
Figure 13:
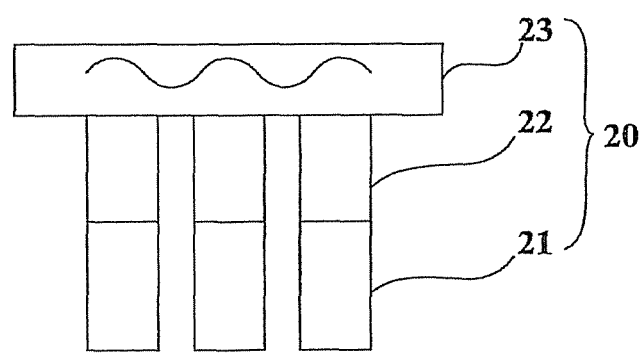
FIG. 13 is a diagram of the acoustic matching layer of the proposed ultrasound probe.

In the case of 2.8/1.2, the specificity will differ from the results of the acoustic impedance of longitudinal waves AI2.0 [Mrayl] (Embodiment 1), and a dip will occur in the directional characteristics (EF) (for example, near 3.7 MHz, 4.8 MHz); therefore, it may be understood that it is not properly functioning as the film-like ML (Indicated by → in FIG. 10B). From this result, the laminated film-like ML is preferably configured with materials in which the variation in the acoustic impedance of longitudinal waves AI is within 20% (refer to FIG. 10A). Within 20%, as mentioned here, corresponds to within the range of 2.4/1.6 (1.6 to 2.4) towards the acoustic impedance of longitudinal waves AI2.0. Furthermore, in the laminated film-like ML, when it is not required to change the acoustic impedance of the longitudinal waves AI, it is further desirable to have the variation in the acoustic impedance of longitudinal waves AI at 0%.

As described above, according to this embodiment, the frequency of the standing waves, in which interference occurs between the film-like ML and the adjacent element, is off-set, the resonance being suppressed. Therefore, aggravation of the specific frequency in sensitivity and directional characteristics (EF) is reduced. Regarding longitudinal waves, the acoustic impedance AI is substantially the same; therefore, it functions as a film-like ML with entire thickness λ/4. As a result, the performance of the ultrasound probe may be improved while maintaining acoustic matching.

In the embodiment mentioned above, the film-like ML was made as a 2-layer structure; however, it may be made as a structure of 3 layers or more. In this case as well, the Poisson's ratio, thickness, and longitudinal wave impedance in each film-like ML is set, simulation similar to those mentioned above is performed, and the Poisson's ratio, etc., may be determined from the results thereof.

Although several embodiments of this invention have been described, the embodiments above are presented as examples and are not intended to limit the scope of the invention. These new embodiments can be practiced in other various forms, with various omissions, substitutions, and changes able to be made without deviating from the summary of the invention. These embodiments and variations thereof are included in the scope and summary of the invention and are also included in the invention described in the scope of the claims and any equivalent thereof.

What is claimed is:

1. An ultrasound probe comprising:
   an ultrasound transducer; and
   a plurality of acoustic matching layers arranged by layering in order of Poisson's ratio values being low to high along the direction of irradiation of the ultrasound waves irradiated from the ultrasound transducer; and wherein the plurality of acoustic matching layers are shaped like a film, each of the acoustic impedance of longitudinal waves of the adjacent acoustic matching layer being substantially same.

2. The ultrasound probe according to claim 1, wherein, in the plurality of acoustic matching layers, the total thickness of each acoustic matching layer is substantially ¼the wavelength.

3. The ultrasound probe according to claim 1, wherein, in the plurality of acoustic matching layers, the thickness ratio of the adjacent acoustic matching later is substantially 1.

4. The ultrasound probe according to claim 1, wherein, the Poisson's ratio of the plurality of acoustic matching layers is within the range of 0.35 to 0.49.

5. The ultrasound probe according to claim 4, wherein, in the plurality of acoustic matching layers, the variation of the Poisson's ratio of the adjacent acoustic matching layer is 3% or more.

6. The ultrasound probe according to claim 1, wherein, the acoustic impedance of longitudinal waves of the plurality of acoustic matching layers is within the range of 159 [$kgm^{-2}s^{-1}$] to 530 [$kgm^{-2}s^{-1}$].

7. The ultrasound probe according to claim 6, wherein, in the plurality of acoustic matching layers, the variation in acoustic impedance of longitudinal waves of adjacent acoustic matching layers is within 20%.

8. The ultrasound probe according to Claim 1, wherein, the plurality of acoustic matching layers is a combination of two or more materials of polyethylene resin, polyurethane resin, polyimide resin, epoxy resin, and polyester resin.

* * * * *